US011000416B2

United States Patent
Marz et al.

(10) Patent No.: US 11,000,416 B2
(45) Date of Patent: May 11, 2021

(54) WOUND DRESSING FOR WOUND TREATMENT IN A DAMP OR WET ENVIRONMENT

(71) Applicant: IVF Hartmann AG, Neuhausen am Rheinfall (CH)

(72) Inventors: Jacqueline Marz, Rielasingen-Worblingen (DE); Markus Rothmaier, Illnau (CH)

(73) Assignee: IVF Hartman AG, Neuhausen am Rheinfall (CH)

( * ) Notice: Subject to any disclaimer, the term of this patent is extended or adjusted under 35 U.S.C. 154(b) by 555 days.

(21) Appl. No.: 15/558,800

(22) PCT Filed: Apr. 4, 2016

(86) PCT No.: PCT/EP2016/057364
§ 371 (c)(1),
(2) Date: Sep. 15, 2017

(87) PCT Pub. No.: WO2016/156619
PCT Pub. Date: Oct. 6, 2016

(65) Prior Publication Data
US 2018/0071147 A1 Mar. 15, 2018

(30) Foreign Application Priority Data
Apr. 2, 2015 (DE) .................. 10 2015 206 083.7

(51) Int. Cl.
*A61F 13/00* (2006.01)
*A61L 15/28* (2006.01)
(Continued)

(52) U.S. Cl.
CPC .. *A61F 13/00042* (2013.01); *A61F 13/00012* (2013.01); *A61F 13/00017* (2013.01);
(Continued)

(58) Field of Classification Search
CPC .......... A61F 13/00017; A61F 13/00029; A61F 13/00063; A61F 13/00068;
(Continued)

(56) References Cited

U.S. PATENT DOCUMENTS 9,050,443 B2  6/2015 Knill et al.
9,707,311 B2  7/2017 Riesinger
(Continued)

FOREIGN PATENT DOCUMENTS

CN  1819808 A  8/2006
CN  103735359 A  * 4/2014  .............. A61L 15/44
(Continued)

OTHER PUBLICATIONS

Machine translation of description and claims EP0594034.
(Continued)

*Primary Examiner* — Tatyana Zalukaeva
*Assistant Examiner* — Heather K Barnwell
(74) *Attorney, Agent, or Firm* — Dilworth & Barrese, LLP

(57) ABSTRACT

The disclosure relates to a wound dressing comprising a fibre fleece-based body, and a packaging forming the outer visible sides of the wound dressing, which packaging contains a layer made from a flat textile on the side of the wound dressing facing the wound, which has an outer-side, partially and structurally applied coating, and wherein the packaging has a fibre fleece layer on the side of the wound dressing facing away from the wound, which forms the outer visible side of the wound dressing; and, a liquid-impermeable plastic film layer on the side of the fibre fleece layer facing the wound, and wherein the fibre fleece layer, the plastic film layer, the body and the textile layer are not connected to one another, but rather lie with the flat sides thereof loosely and (Continued)

movably against one another and are only connected along the peripheral edges by a joint connection.

19 Claims, 1 Drawing Sheet

(51) Int. Cl.
| | | |
|---|---|---|
| *A61L 15/60* | (2006.01) | |
| *B29C 65/08* | (2006.01) | |
| *B29C 65/00* | (2006.01) | |
| *A61L 15/26* | (2006.01) | |
| *B29L 9/00* | (2006.01) | |

(52) U.S. Cl.
CPC .. *A61F 13/00029* (2013.01); *A61F 13/00063* (2013.01); *A61F 13/00068* (2013.01); *A61L 15/26* (2013.01); *A61L 15/28* (2013.01); *A61L 15/60* (2013.01); *A61F 2013/0017* (2013.01); *A61F 2013/0091* (2013.01); *A61F 2013/00217* (2013.01); *A61F 2013/00238* (2013.01); *A61F 2013/00727* (2013.01); *A61F 2013/00744* (2013.01); *A61F 2013/00753* (2013.01); *A61F 2013/00855* (2013.01); *A61L 2420/08* (2013.01); *B29C 65/08* (2013.01); *B29C 66/43* (2013.01); *B29L 2009/00* (2013.01)

(58) Field of Classification Search
CPC ...... A61F 2013/00361; A61F 13/00012; A61F 2013/00217; A61F 2013/00753; A61F 2013/00727; A61F 13/00042; A61L 15/60; A61L 15/26
See application file for complete search history.

(56) References Cited

U.S. PATENT DOCUMENTS

| | | |
|---|---|---|
| 2008/0082059 A1 | 4/2008 | Fink et al. |
| 2010/0030170 A1* | 2/2010 | Keller .................. A61F 13/533 604/360 |
| 2011/0171277 A1* | 7/2011 | Schonberger ........ C08G 18/753 424/401 |
| 2012/0010584 A1 | 1/2012 | Schmidt |
| 2013/0231623 A1* | 9/2013 | Richard ............ A61F 13/00029 604/372 |
| 2014/0163485 A1* | 6/2014 | Knill ...................... A61L 15/46 604/304 |
| 2014/0180187 A1* | 6/2014 | Croizat .................. A61L 15/20 602/45 |
| 2016/0317353 A1* | 11/2016 | Wang ................ A61F 13/00017 |

FOREIGN PATENT DOCUMENTS

| | | | |
|---|---|---|---|
| DE | 102010020050 A1 | 11/2011 | |
| EP | 0594034 A1 * | 4/1994 | ....... A61F 13/00021 |
| EP | 0594034 B1 * | 1/1997 | ....... A61F 13/00021 |
| EP | 0594034 B1 | 1/1997 | |
| EP | 2404581 A2 | 1/2012 | |
| WO | 2005007026 A2 | 1/2005 | |
| WO | 03039602 A2 | 5/2005 | |
| WO | 2009019224 A2 | 2/2009 | |
| WO | 2009019229 A2 | 2/2009 | |
| WO | 2010024928 A1 | 3/2010 | |
| WO | 2011141454 A1 | 11/2011 | |
| WO | WO-2011141454 A1 * | 11/2011 | ............. A61L 15/46 |

OTHER PUBLICATIONS

English Translation of Written Opinion from PCT/EP2016/057364 dated Jul. 5, 2016.
Third Office Communication from Chinese Application No. 201680004232.1 dated Mar. 3, 2021.

* cited by examiner

WOUND DRESSING FOR WOUND TREATMENT IN A DAMP OR WET ENVIRONMENT

This application claims priority German Patent Application No. 102015206083.7 filed on Apr. 2, 2015.

The invention relates to a wound dressing for wound treatment in a moist or moist/wet environment, having a fibrous nonwoven-based suction/rinsing body in which superabsorbent material is incorporated in a distributed manner, a saline aqueous solution, especially Ringer's solution, which preferably contains a substance with antimicrobial action, having been applied to the suction/rinsing body by the manufacturer, and having a cover forming the outer visual sides of the wound dressing, the cover comprising on the wound-facing side of the wound dressing a layer composed of a textile planar material, especially composed of a weft-knitted fabric, warp-knitted fabric or woven fabric, the layer composed of a textile planar material having on the wound-facing side a coating, preferably composed of silicone, which has been applied on the outer side in a partial and structured manner and which acts atraumatically, having a degree of coverage of at most 70%.

Such a wound dressing is known from WO 2011/141454 A1 or EP 0 594 034 B1 from the applicant. Here, the wound dressing is a wound pad-type or compress-type wound dressing which is applicable to a wound or can even be used for packing deep wounds. The manufacturer applies to the suction/rinsing body, especially up to saturation, a saline aqueous solution, which swells the superabsorbent material and lets it pass into a gelatinous state. This gives the suction/rinsing body a dual function in the case of wounds exhibiting severe exudation. Wound secretions, including their critical constituents such as pathogens, are actively taken up by the suction/rinsing body and held therein, and, at the same time, the suction/rinsing body releases in return the saline aqueous solution to the wound and thus creates or supports a moist wound environment. This supports wound cleaning and a positive wound conditioning and thus positively influences healing. This is referred to as interactive wet therapy, which is preferably used especially in the case of poorly healing wounds, in the case of clinically manifestly infected wounds or in the case of chronic wounds of differing etiology, such as diabetic gangrene, decubitus ulcers or venous ulcers.

The aforementioned Ringer's solution is typically an aqueous solution containing sodium chloride, potassium chloride and calcium chloride (especially 8.6 g of NaCl, 0.3 g of KCl and 0.33 g of $CaCl_2$ per lite).

The change interval time, i.e., the usage time of a wound dressing until the next bandage change, is supposed to be at least 24 h, though there are efforts to increase the change interval time, especially to from 48 to 72 h. This would be desirable from economical points of view, but also for reasons of an interference of wound healing that is caused by frequent bandage change.

US 2008/0082059 A1 mentions a wound dressing which is integrated into a negative-pressure wound bandage and which has a suction body, for which various lists mention a multiplicity of substances and substance additives, especially a plurality of carrier substances, a plurality of substance additives, including polyhexamethylene biguanide and isotonic saline solution. A specific composition of the suction body and its cover is not disclosed. WO 2010/024928 A1 discloses a composite comprising a film layer, a collagen layer and a hydrogel layer containing polyhexamethylene biguanide. WO 2003/039602 A2 teaches, in the case of a material for the uptake of wound exudate, covalently bonding antimicrobially acting groups to a support polymer and localizing them as a result.

It is an object of the present invention to improve a wound dressing of the type described at the start with respect to its economical manufacturability. Furthermore, the intention is to improve its drapeability and flexibility.

This object is, in the case of a wound dressing, achieved according to the invention by the cover comprising a fibrous nonwoven layer on the side of the wound dressing that faces away from the wound, which fibrous nonwoven layer forms the outer visual side of the wound dressing that faces away from the wound, and by a fluid-impermeable plastics film layer being arranged on the wound-facing side of said fibrous nonwoven layer, and by the fibrous nonwoven layer, the plastics film layer, the suction/rinsing body and the layer composed of textile planar material not being joined to another in a planar manner, but being in contact with one another via their planar sides in a loose and slidable manner, the fibrous nonwoven layer, the plastics film layer, the suction/rinsing body and the layer composed of textile planar material being joined to one another only along their peripheral edge by means of a joint.

Because the outer visual side of the wound dressing that faces away from the wound is not formed by a plastics film layer, as in the case of the already known product, but by a fibrous web layer, the tactile and haptic grippability of the wound dressing is improved, even by means of instruments, since the fibrous web layer is less slippery than a plastics film layer, but can definitely be referred to as nonslip even in the wet state. Furthermore, the sensation, especially in contact with the fingers of the caregiver and with the body surface of the patient, is improved and found to be more pleasant. Furthermore, it proves to be advantageous that the flexibility and the drapeability of the wound dressing according to the invention is improved. It was found that, surprisingly, the plastics film layer arranged not externally, but on the wound-facing side of the fibrous web layer, does not impede the flexibility and drapeability of the wound dressing, and this is also due to the fact that the layers are not joined to one another in a planar manner, but only along their edge, meaning that they are, according to the invention, in contact with one another via their planar sides only in a loose and slidable manner. Furthermore, it has proved to be particularly advantageous that the, as intended, permanent joining of the layers only along their peripheral edge can be used at the same time for singularizing the individual wound dressings from larger planar material arrangements in the course of production. The production of this edge-side joint between preferably all layers within the wound dressing is thus utilized at the same time for the production of the separation cut or singularization cut or separation process or singularization process.

Advantageously, this joint between the layers, which joint is intended only at the edge, can be formed by an ultrasonic welded joint or a laser welded joint. The ultrasonic or laser welded joint can comprise a succession of discrete welded points. However, said welded points can also be arranged successively in an almost continuous manner such that the impression of a continuous joint line arises visually.

The mentioned visual-side fibrous nonwoven layer can be formed from thermoplastic fiber material, especially from polyolefin, especially from polypropylene.

The surface weight of the fibrous nonwoven layer on the side of the wound dressing that faces away from the wound is preferably 15-100 $g/m^2$, preferably 20-60 $g/m^2$, particularly preferably 25-40 $g/m^2$. It may be advantageous to position two especially identical material plies of a fibrous nonwoven material on top of one another, preferably having a surface weight of 25-40 g/m² in each case, as the fibrous nonwoven layer. In this way, it is possible to increase process reliability in the formation of the edge-side joint.

Furthermore, it proves to be advantageous when the density of the fibrous nonwoven layer on the side of the wound dressing that faces away from the wound is 10-1000 kg/m³, preferably 50-250 kg/m², particularly preferably 100-150 kg/m³.

Furthermore, it proves to be advantageous when the fluid-impermeable plastics film layer is formed from a thermoplastic material, especially from polyolefin, especially from polypropylene.

Furthermore, it proves to be advantageous when the fluid-impermeable plastics film layer has a surface weight of 5-100 g/m², preferably 8-50 g/m², particularly preferably 10-25 g/m², and a thickness of 5-100 µm, preferably 8-50 µm, particularly preferably 10-25 µm.

It proves to be advantageous when the fibrous nonwoven-based suction/rinsing body comprises cellulosic fibers, especially a mixture of cellulosic fibers and thermoplastic fibers, especially polyolefin fibers, especially polypropylene fibers or polypropylene/polyethylene fibers.

In this connection, the surface weight of the fiber fraction of the suction/rinsing body is advantageously from 20 to 500 g/m², preferably 30-300 g/m², particularly preferably 30-200 g/m², especially 30-150 g/m².

It proves to be advantageous when the density of the fiber fraction of the suction/rinsing body is 20-500 kg/m³, preferably 30-300 kg/m', particularly preferably 50-200 kg/m³. Furthermore, it proves to be advantageous when the layer composed of textile planar material is formed from a thermoplastic material, especially from polyolefin, especially from polypropylene.

Furthermore, it proves to be advantageous when the degree of coverage of the coating which has been applied in a partial and structured manner and which acts atraumatically is 20-70%, especially 25-50%, especially 30-40%.

It proves to be further advantageous when the coating which has been applied in a partial and structured manner and which acts atraumatically is in the form of strips. In this connection, the strips can be extended linearly. They preferably run in parallel or equidistantly to one another. The width of a strip is advantageously from 1 to 3 mm. The distance of the strips from one another is advantageously from 4 to 8 mm, especially from 4 to 6 mm.

Furthermore, it proves to be advantageous when the wound dressing is designed such that the superabsorbent material is anionic and has negative groups and that the aqueous solution comprises a substance with antimicrobial action, which is silver cations, biguanide or biguanide derivatives, polyguanidines, N-octyl-1-[10-(4-octyliminopyridin-1-yl)decyl]pyridin-4-imine (octenidine), quaternary ammonium compounds, triazines or the ammonium compound tauroline, and that said substance with antimicrobial action is cationically charged at pH levels of 4-7.5 of a typical moist or moist/wet wound environment and is therefore attracted by negative groups of the anionic super absorbent material and thus acts antimicrobially within the suction/rinsing body. The surface weight of the superabsorbent material within the suction/rinsing body is preferably 30-150 g/m², especially 50-100 g/m², especially 60-80 g/m².

According to a further inventive concept of particular significance, it is proposed to design the wound dressing such that the thickness of the wound dressing in the saline aqueous solution-applied state is 3-7 mm, especially 4-6 mm. It is assumed here that the thickness of the fibrous nonwoven layer which faces away from the wound and of the underlying plastics film layer and also the thickness of the wound-facing layer composed of textile planar material with the atraumatic coating which has been applied in a partial and structured manner account for at most 1 mm of the total thickness of the manufacturer-wetted wound dressing, meaning that the remainder arises from the fluid-storing suction/rinsing body. Compared to already known wound dressings for moist/wet wound therapy, the wound dressing as designed above is of a distinctly lower thickness. It has been found that, surprisingly, the absorption behavior for wound exudates is, however, not lowered. A possible, but not yet proven, explanation therefor would be that a surface layer of the suction/rinsing body is substantially responsible for the absorption of wound exudate in the suction/rinsing body activated with saline aqueous solution. This inherently surprising property opens the possibility of working with lower surface weights of the components of the suction/rinsing body, and this in turn reduces overall the thickness of the wound dressing and improves its flexibility and drapeability.

Further protection is claimed for a method for producing a wound dressing according to the invention, characterized in that the fibrous nonwoven layer, the fluid-impermeable plastics film layer, a layer forming the fibrous nonwoven-based suction/rinsing body, and the layer composed of textile planar material are fed as respectively continuous planar materials and arranged on top of one another in the stated sequence of layers and in that the layers are joined to one another only along their peripheral edge and, at the same time, the wound dressings are singularized from the planar materials.

As already mentioned at the start, the joining of the layers can be advantageously carried out by ultrasonic or laser welding.

Further features, details and advantages of the invention are revealed by the attached claims and by the graphic depiction and following description of a preferred embodiment of the invention. In the drawing:

Figure 1:
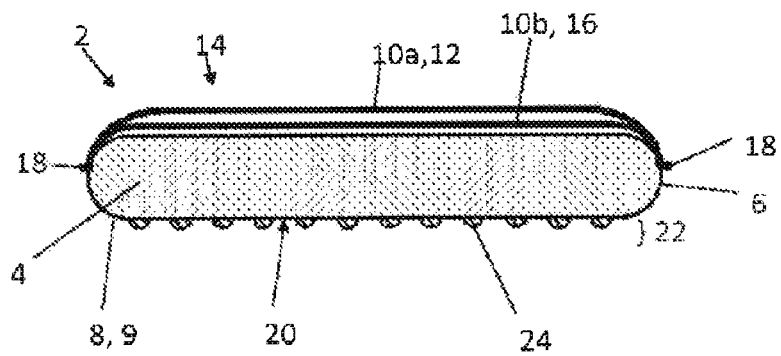
FIG. 1 shows a schematic sectional view of a wound dressing according to the invention.

FIG. 1 shows a sectional view of a wound dressing 2, It comprises a suction/rinsing body 4 based on a fibrous nonwoven. This fiber base is a preferred mixture of airlaid cellulose fibers (pulp) and polypropylene fibers or polypropylene/polyethylene fibers. Superabsorbent polymer materials (SAP) in particle form or in fiber form are admixed with this fiber mixture as homogeneously as possible, the SAP fraction of the total mass of the suction/rinsing body 4 preferably being 40-50% by weight. The mean particle size of the SAP particles is, for example, from 150 to 850 (e.g., the polyacrylate brand Favor pac 300 from Evonik Stockhausen GmbH).

The suction/rinsing body 4 is surrounded by a cover 6 which forms the outer sides of the wound dressing and which is formed by a shell layer 8 which faces the wound and two shell layers 10a, b which face away from the wound. The shell layer 8 which faces the wound is preferably a layer 9 composed of a textile planar material, such as a weft-knitted fabric, preferably composed of polypropylene, though a woven fabric or warp-knitted fabric would also be advantageously conceivable, i.e., a shell layer composed of threads or filaments with textile interlacing, which allows a good fluid exchange between the suction/rinsing body 4 and the wound environment.

The one shell layer 10*a* which faces away from the wound is a fibrous web layer 12, preferably composed of polypropylene, which forms a visual side 14 of the wound dressing 2, which visual side faces away from the wound. The second shell layer 10*b* is formed by a fluid-impermeable plastics film layer 16 which is arranged immediately below the fibrous web layer 12, i.e., on the wound-facing side of the fibrous web layer 12, between the fibrous web layer 12 and the suction/rinsing body 4. These two shell layers 10*a*, 10*b* which face away from the wound are not joined to one another in a planar manner; thus, they do not form a laminate in the proper sense, but are in planar contact with one another in a loose and slidable manner, though they are joined to one another and to the further components of the wound dressing along a peripheral edge 18 or a peripheral edge region. To this end, the layers of the wound dressing are fed as planar materials which are each continuous in one machine direction and said layers are arranged on top of one another. Thus, these are the fibrous web layer 12, the plastics film layer 16, a fibrous web layer with superabsorbent polymer materials, which forms the actual fibrous web-based suction/rinsing body, and the wound-facing layer composed of a textile planar material. To delimit, define and ultimately singularize the wound dressing products, there is produced, perpendicular to the layer plane, a joint which includes all the layers, preferably in the form of an ultrasonic welded joint. In the course of the production of said ultrasonic welded joint, or afterwards, but along the joining region of this joint, the individual wound dressing products are then singularized. The width of the joint transverse to its longitudinal extent is preferably very low, meaning that a barely perceptible, laterally minimally protruding product edge is perceptible on the finished singularized product. When saline aqueous solution, especially Ringer's solution, is lastly applied to the wound dressing by the manufacturer, the shell layer 8 which faces away from towards the wound and the shell layers 10*a, b* which face the wound are stretched away from one another as a result of swelling of the suction/rinsing body 4, giving rise to the impression of a highly planar, peripherally rounded wound pad.

Before the application of saline aqueous solution, a coating 22 which is applied in a partial and structured manner and which acts atraumatically is provided on the wound-facing outer side 20 of the wound-facing shell layer 8. Said coating 22 is preferably a silicone coating, the coating being formed porously and, in the case depicted by way of example, by a plurality of comparatively thin strips 24 or lines or island-shaped regions, which are separated from one another by noncoated regions. In said noncoated regions, the wound-facing shell layer 8 is exposed to the wound. In this respect, the atraumatically acting coating 22 forms a projection in the order of magnitude stated in the introduction to the description, resulting in, firstly, it being possible to prevent the shell layer 8 adhesively bonding to wound tissue and, secondly, it being possible to maintain a certain minimal distance between the wound-facing shell layer 8 and the wound tissue, resulting in the porous shell layer material remaining open in a three-dimensional manner and providing or maintaining a relatively low resistance for the passage of fluid in both directions over the service life of the wound dressing.

The above-described atraumatically acting coating can be provided in the wound-facing shell layer 8 either before or after the singularization of the wound dressing products. To this end, it is possible to use a dispensing machine of the type described in WO 2011/141454 A1, Only afterwards is saline aqueous solution applied to the now singularized wound dressings. Added to said saline solution is a substance with antimicrobial action, which substance is cationic in a moist or moist/wet wound environment at pH levels in the slightly acidic to neutral range from pH 4 to 7.5. This cationic substance with antimicrobial action is attracted by negative groups of the anionic superabsorbent material such that it, even in the fluid-exchanging operation of the suction/rinsing body 4, remains bound to the superabsorbent materials, i.e., is as far as possible not released into the wound environment. This prevents a multiplication of pathogens introduced into the suction/rinsing body 4 with wound secretion, and, as a result, a reverse contamination in the direction of the wound is prevented as far as possible. It has been found that such a microbiological reverse contamination could be prevented as far as possible for 72 h, and this is due to the fact that the antimicrobially acting substance, owing to its cationic state, is held in an evenly distributed manner within the suction/rinsing body 4 in connection with the superabsorbent materials.

In an exemplary preferred composition of the wound dressing 2, the fibrous nonwoven base of the suction/rinsing body 4 consists of 33 g/m$^2$ cellulose fibers (pulp), 11 g/m$^2$ polypropylene/polyethylene fibers as binding fibers. 70 g/m$^2$ of the aforementioned superabsorbent polymer materials (SAP) are homogeneously admixed with this fiber mixture. Moreover, the thus obtained mixture (fibrous nonwoven base SAP), which forms the suction/rinsing, body 4, can be surrounded by a cellulosic tissue layer, especially of a surface weight of, by way of example, 17 g/m$^2$ on each side (not depicted in the figure); however, this is not absolutely necessary. The wound dressing can, by way of example, be round, having an exemplary dimension of the suction/rinsing body 4, which substantially corresponds to the dimension of the wound dressing 2, of diameter 5.5 cm. Lastly, the wound dressing 2 has been activated with 8 ml of Ringer's solution, this substantially corresponding here to a saturation of the suction/rinsing body with fluid. The cover 6 is as described above.

Figure 2:
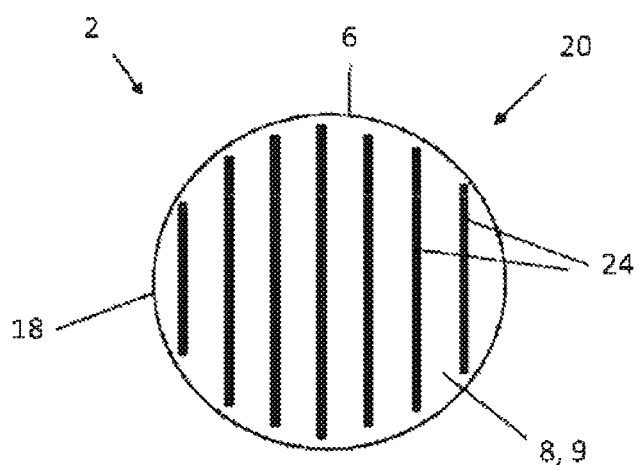
FIG. 2 shows a view of the wound dressing with a look at the wound-facing side of the wound dressing.

FIG. 2 clarifies the partial and structured application of the atraumatic coating 22, which is applied as strips, i.e., in the form of strips 24, using the parameters specified at the start.

The invention claimed is:

1. A wound dressing (2) for wound treatment in a moist or moist/wet environment, comprising:
   a fibrous web-based suction-rinsing body (4) comprising a mixture of superabsorbent material which is incorporated in a distributed manner, cellulosic fibers and thermoplastic fibers, and wherein within the suction-rinsing body (4) there is a saline aqueous solution, and wherein the suction-rinsing (4) is surrounded by a cellulosic tissue layer and
   a cover (6) forming outer visual sides of the wound dressing, wherein the cover (6) comprises, on a wound-facing side of the wound dressing, a layer (9) comprising a textile planar material, wherein the layer (9) comprising the textile planar material has, on the wound-facing side, a coating (22), present on an outer side in a partial and structured manner and which acts atraumatically, and which has a degree of coverage of at most 70%, and wherein the cover (6) further comprises a fibrous nonwoven web layer (12) on a side of the wound dressing that faces away from the wound, wherein the fibrous nonwoven web layer forms an outer visual side of the wound dressing that faces away from the wound, and wherein a fluid-impermeable plastics film layer (16) is arranged on the wound-facing side of said fibrous nonwoven web layer (12), and wherein the fibrous nonwoven web layer (12), the plastics film layer (16), the suction-rinsing body (4) and the layer (9) composed of textile planar material are not joined to another in a planar manner, but are in contact with one another via planar sides in a loose and slidable manner, the fibrous nonwoven web layer (12), the plastics film layer (16), the suction-rinsing body (4) and the layer (9) composed of textile planar material being joined to one another only along a peripheral edge (18) by means of a joint.

2. The wound dressing of claim 1, wherein the joint is an ultrasonic welded joint.

3. The wound dressing of claim 2, wherein the ultrasonic welded joint comprises a succession of discrete ultrasonic welded points.

4. The wound dressing of claim 1 wherein the fibrous nonwoven web layer (12) is formed from thermoplastic fiber material.

5. The wound dressing of claim 1 wherein a surface weight of the fibrous nonwoven web layer (12) is 15-100 g/m$^2$.

6. The wound dressing of claim 1 wherein a density of the fibrous nonwoven web layer (12) is 10-1000 kg/m$^3$.

7. The wound dressing of claim 1 wherein the fluid-impermeable plastics film layer (16) is formed from a thermoplastic material.

8. The wound dressing of claim 1 wherein the fluid-impermeable plastics film layer (16) has a surface weight of 5-100 g/m$^2$ and a thickness of 5-100 μm.

9. The wound dressing of claim 1 wherein a surface weight of a fiber fraction of the suction-rinsing body (4) is 20-500 g/m$^2$.

10. The wound dressing of claim 1 wherein a density of a fiber fraction of the suction-rinsing body (4) is 20-500 kg/m$^3$.

11. The wound dressing of claim 1 wherein the layer (9) composed of textile planar material is formed from a thermoplastic material.

12. The wound dressing of claim 1 wherein the degree of coverage of the coating (22) which has been applied in a partial and structured manner and which acts atraumatically, is 20-70%.

13. The wound dressing of claim 1 wherein the coating (22) which has been applied in a partial and structured manner and which acts atraumatically, is in a form of strips (24).

14. The wound dressing of claim 13, wherein a width of the strips (24) is 1-3 mm and/or a distance of the strips (24) from one another is 4-8 mm.

15. The wound dressing of claim 1 wherein a surface weight of a fiber fraction of the fibrous web-based suction-rinsing body (4) is 30-100 g/m$^2$ and in that the surface weight of the superabsorbent material within the fibrous web-based suction-rinsing body (4) is 50-100 g/m$^2$ and in that a thickness of the wound dressing in a saline aqueous solution-applied state is 3-7 mm.

16. The wound dressing of claim 1 wherein the saline aqueous solution is Ringer's solution.

17. The wound dressing of claim 1 wherein the textile planar material of layer (9) is selected from the group consisting of weft-knitted fabric, warp-knitted fabric and woven fabric.

18. The wound dressing of claim 1 wherein the coating (22) comprises silicone.

19. A method for producing wound dressings (2) of claim 1 comprising feeding the fibrous nonwoven web layer (12), the fluid-impermeable plastics film layer (16), the layer forming the fibrous web-based suction-rinsing body (4) surrounded by the cellulosic tissue layer, and the layer (9) composed of textile planar material as respectively continuous planar materials which are arranged on top of one another in the stated sequence of layers and in that the layers are joined to one another only along the peripheral edge (18), and, at the same time, wherein the wound dressings (2) are singularized from the planar materials.

\* \* \* \* \*